United States Patent
Hagihara et al.

(10) Patent No.: US 11,744,438 B2
(45) Date of Patent: Sep. 5, 2023

(54) IMAGE PROCESSING DEVICE FOR ENDOSCOPE, ENDOSCOPE DEVICE, IMAGE PROCESSING METHOD OF IMAGE PROCESSING DEVICE FOR ENDOSCOPE, AND IMAGE PROCESSING PROGRAM

(71) Applicant: Sony Olympus Medical Solutions Inc., Tokyo (JP)

(72) Inventors: Masahiro Hagihara, Tokyo (JP); Morinao Fukuoka, Kanagawa (JP); Yuichi Yamada, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 366 days.

(21) Appl. No.: 16/907,333

(22) Filed: Jun. 22, 2020

(65) Prior Publication Data

US 2020/0315425 A1    Oct. 8, 2020

Related U.S. Application Data

(63) Continuation of application No. 15/710,207, filed on Sep. 20, 2017, now Pat. No. 10,729,308.

(51) Int. Cl.
  *A61B 1/00*    (2006.01)
  *A61B 1/04*    (2006.01)
  *H04N 23/68*    (2023.01)

(52) U.S. Cl.
  CPC ...... *A61B 1/00009* (2013.01); *A61B 1/00045* (2013.01); *A61B 1/00048* (2013.01); *A61B 1/00105* (2013.01); *A61B 1/04* (2013.01); *A61B 1/042* (2013.01); *A61B 1/0005* (2013.01); *A61B 1/00188* (2013.01); *H04N 23/683* (2023.01)

(58) Field of Classification Search
  CPC ............ A61B 1/00009; A61B 1/00045; A61B 1/00048; A61B 1/00188
  See application file for complete search history.

(56) References Cited

U.S. PATENT DOCUMENTS

| | | |
|---|---|---|
| 2002/0033836 A1 | 3/2002 | Smith |
| 2003/0025789 A1 | 2/2003 | Saito et al. |
| 2003/0078477 A1 | 4/2003 | Kang et al. |
| 2004/0201595 A1 | 10/2004 | Manchester |
| 2004/0263424 A1 | 12/2004 | Okuley |

FOREIGN PATENT DOCUMENTS

| | | |
|---|---|---|
| JP | 2004-334 | 1/2004 |
| JP | 2004-240118 A | 8/2004 |
| JP | 2007-33960 A | 2/2007 |
| JP | 2010-85823 A | 4/2010 |
| JP | 2013-20532 A | 1/2013 |
| JP | 2014-72702 A | 4/2014 |

*Primary Examiner* — Aaron B Fairchild
(74) *Attorney, Agent, or Firm* — XSENSUS LLP

(57) ABSTRACT

An image processing device for an endoscope outputs a video signal to an image display part that displays an observation image based on the video signal. The image display part is configured such that a first side of a display screen that displays the observation image is shorter than a second side intersecting with the first side, and is configured to be set in both a first setting state in which the first side is along a vertical direction and a second setting state in which the second side is along the vertical direction. The image processing device includes: a setting state recognition part configured to recognize the setting state; and a video signal generation part configured to generate the video signal such that the subject image in the observation image has an orientation corresponding to the setting state of the image display part.

10 Claims, 17 Drawing Sheets

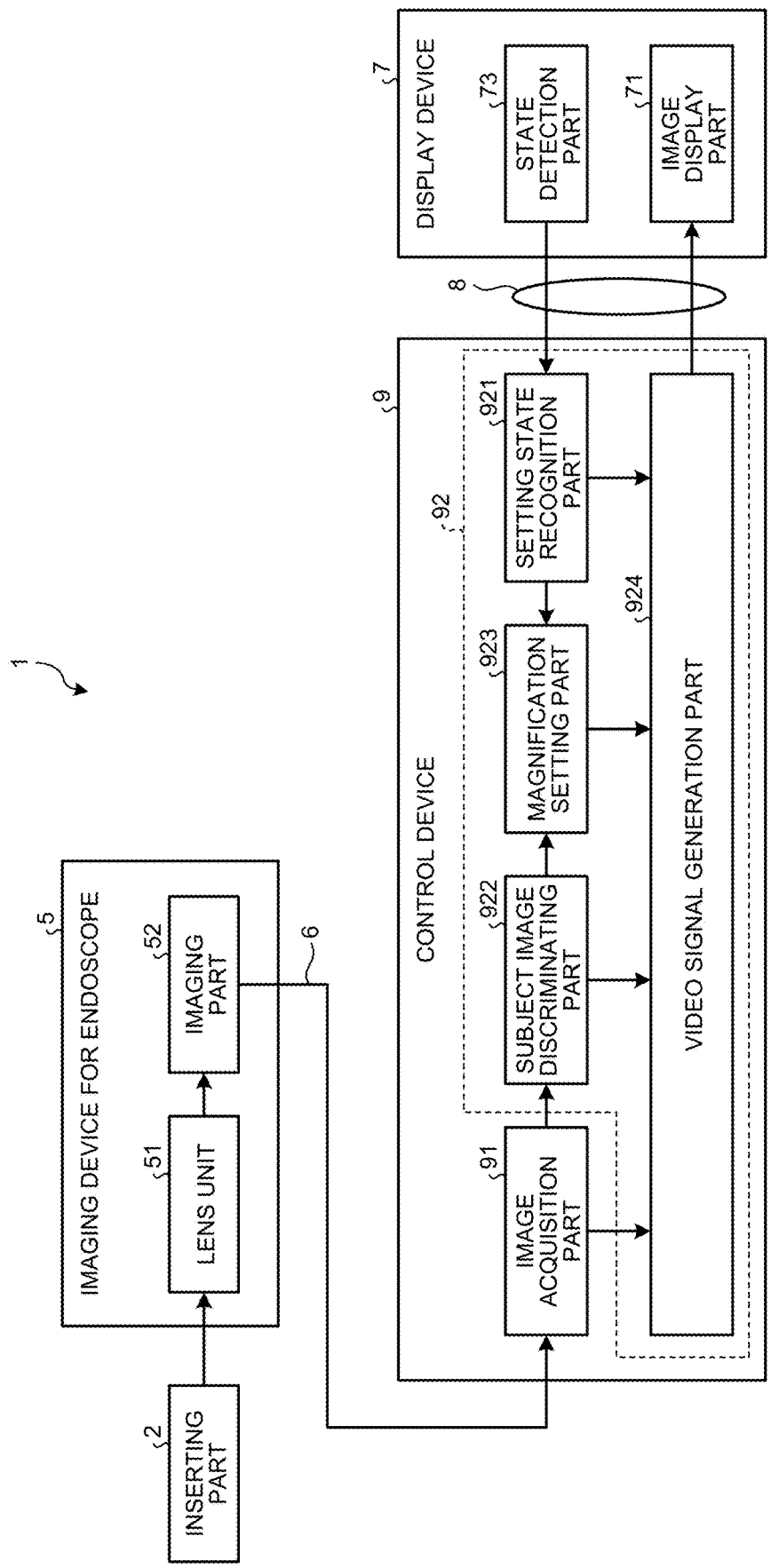

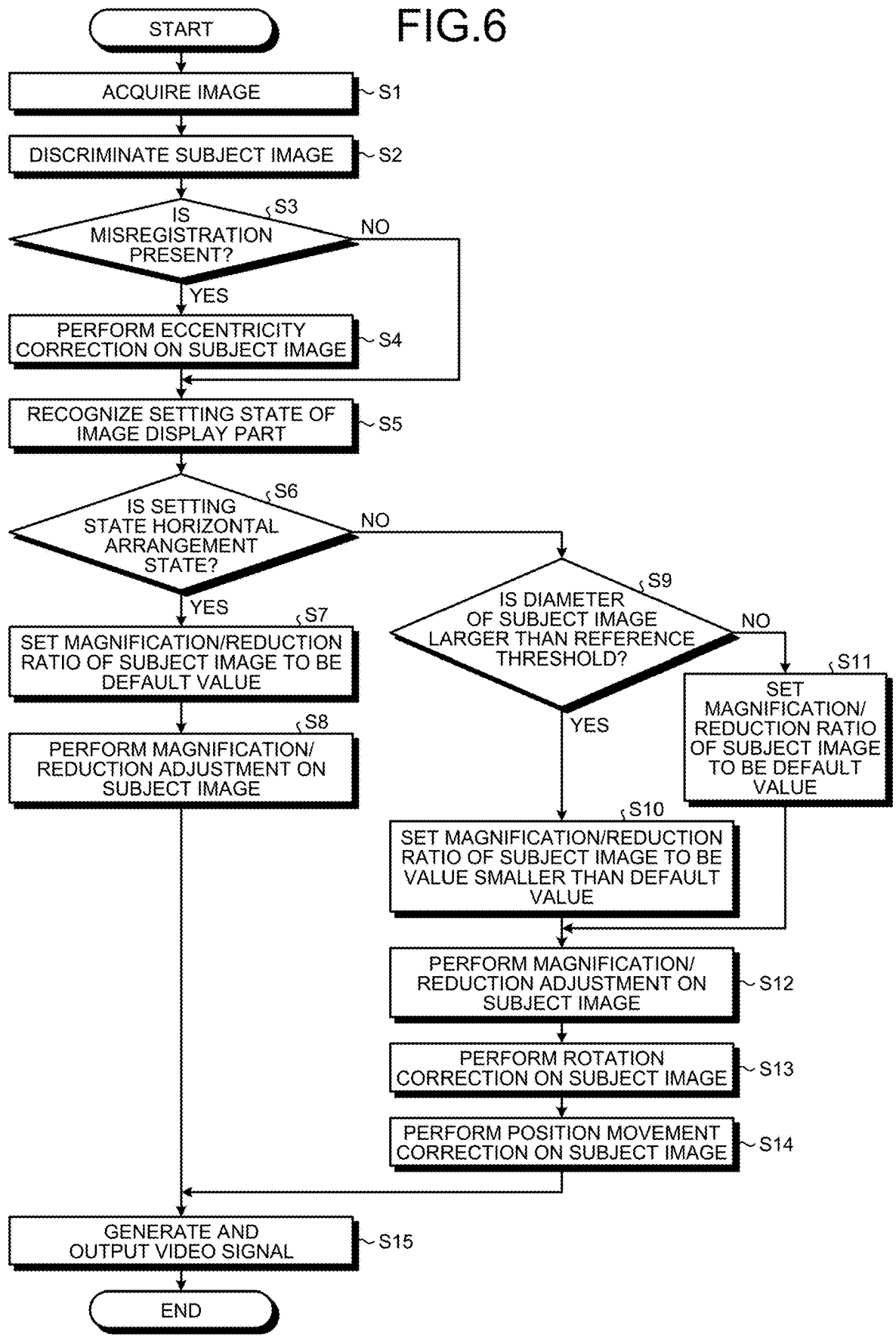

IMAGE PROCESSING DEVICE FOR ENDOSCOPE, ENDOSCOPE DEVICE, IMAGE PROCESSING METHOD OF IMAGE PROCESSING DEVICE FOR ENDOSCOPE, AND IMAGE PROCESSING PROGRAM

CROSS-REFERENCE TO RELATED APPLICATIONS

The present application is a continuation of U.S. application Ser. No. 15/710,207, filed Sep. 20, 2017, which claims priority to JP 2016-198383, filed Oct. 6, 2016, the entire contents of each are incorporated herein by reference.

BACKGROUND

The present disclosure relates to an image processing device for an endoscope, an endoscope device, an image processing method of the image processing device for an endoscope, and an image processing program.

In the related art of a medical field, there is known an endoscope device for imaging a subject such as the inside of a living body using an imaging element to observe the subject (for example, refer to Japanese Laid-open Patent Publication No. 2004-000334 (FIG. 7)).

FIG. 12 is a diagram illustrating a configuration of an endoscope device 100 in the related art. Specifically, FIG. 12 is a diagram illustrating an example of a layout of an operating room for performing an operation using the endoscope device 100 in the related art.

As illustrated in FIG. 12, the endoscope device 100 (medical device) disclosed in Japanese Laid-open Patent Publication No. 2004-000334 (FIG. 7) includes: an endoscope 101 that is inserted into a subject SB to capture a subject image; an imaging device 102 for an endoscope (camera head) that is detachably connected to an eyepiece part of the endoscope 101 and takes the subject image to generate a taken image; a control device 103 (video processor device) that processes the taken image taken by the imaging device 102 for an endoscope to generate a video signal; and a display device 104 (monitor device) that displays an observation image based on the video signal processed by the control device 103.

FIG. 12 illustrates a situation in which an assistant D3 inserts the endoscope 101 into the subject SB lying down in a recumbent position on a bed BD through one side of his/her flank, and a surgical operator D1 performs an operation on the subject SB using an electric scalpel device 202 while observing an observation image displayed on the display device 104.

As illustrated in FIG. 12, a plurality of tool tables 201, the electric scalpel device 202, an anesthetic device 203, a peripheral device 204, and the like are arranged around the bed BD in addition to the control device 103 and the display device 104. The surgical operator D1, an assistant D2, the assistant D3, a nurse D4, and an anesthesiologist D5 stand in a space around the bed BD avoiding the members 103, 104, and 201 to 204 described above.

SUMMARY

In recent years, there is a trend to use the display device 104 configured to have a large screen size of 40 inches or more for the endoscope device 100.

In a case in which the display device 104 configured to have a large screen size is arranged, the width of the display device 104 is particularly large, which obstructs a path of flow of a person standing in the vicinity of the display device 104 (in the example of FIG. 12, a path of flow of the assistant D2 to leave the vicinity of the bed BD).

That is, the path of flow of the person may not be secured unless a setting place of the display device 104 and the like is changed. After the path of flow of the person is secured, the display device 104 and the like need to be moved back to an original setting place (in the example of FIG. 12, a place where the surgical operator D1 may easily observe the observation image).

Thus, there is a problem in that cumbersome work is required in moving the setting place of the display device 104 and the like, and convenience may not be improved.

An image processing device for an endoscope according to one aspect of the present disclosure may process a taken image including a subject image captured by an endoscope to generate a video signal, and output the video signal to an image display part that displays an observation image based on the video signal, wherein the image display part is configured such that a first side of a display screen that displays the observation image is shorter than a second side intersecting with the first side, and is configured to be set in both a first setting state in which the first side is along a vertical direction and a second setting state in which the second side is along the vertical direction, and may include: a setting state recognition part configured to recognize whether the image display part is set in the first setting state or the second setting state; and a video signal generation part configured to generate the video signal such that the subject image in the observation image has an orientation corresponding to the setting state of the image display part.

BRIEF DESCRIPTION OF THE DRAWINGS

FIG. 2 is a block diagram illustrating a configuration of the endoscope device;

FIG. 6 is a flowchart illustrating an operation of an image processing device for an endoscope;

DETAILED DESCRIPTION

Figure 1:
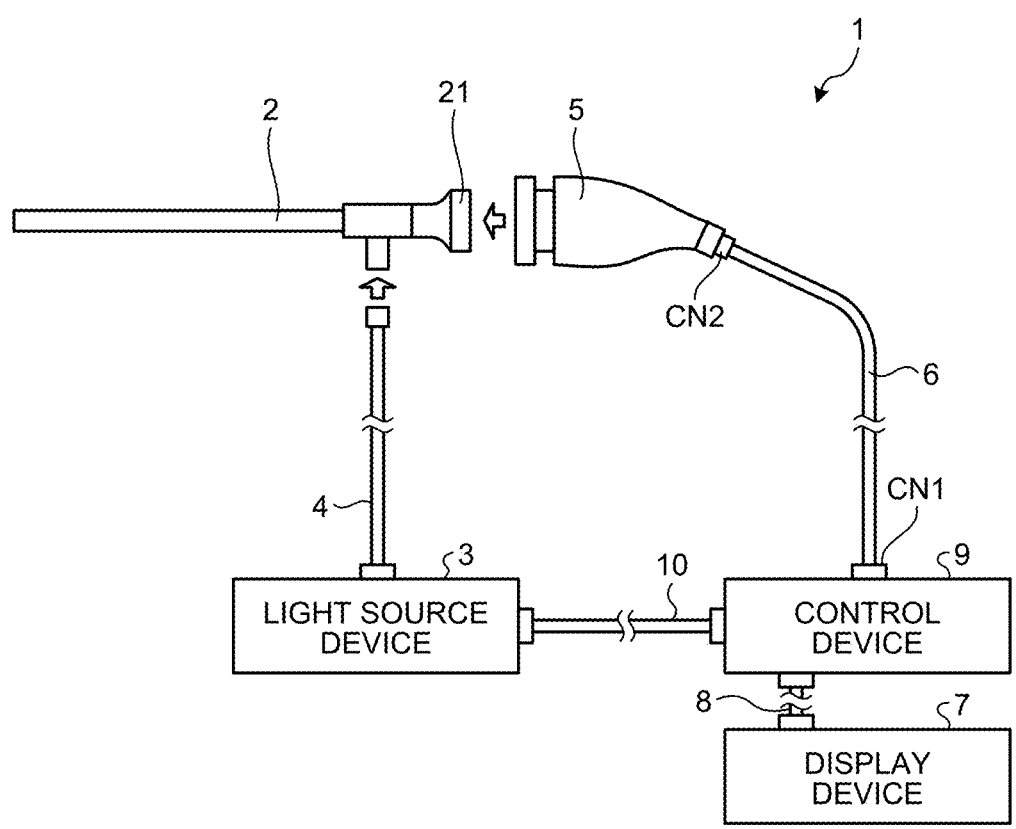
FIG. 1 is a diagram illustrating a schematic configuration of an endoscope device according to a first embodiment of the present disclosure.

The following describes modes for carrying out the present disclosure (hereinafter, referred to as embodiments) with reference to the drawings. The present disclosure is not limited to the embodiments described below. The same component is denoted by the same reference numeral throughout description about the drawings.

First Embodiment

Schematic Configuration of Endoscope Device

FIG. 1 is a diagram illustrating a schematic configuration of an endoscope device 1 according to a first embodiment of the present disclosure. FIG. 2 is a block diagram illustrating a configuration of the endoscope device 1. For convenience of explanation, FIG. 2 does not illustrate a light source device 3, a light guide 4, and a third transmission cable 10.

The endoscope device 1 is a device used in a medical field for observing a subject such as the inside of a living body. As illustrated in FIG. 1 or FIG. 2, the endoscope device 1 includes an inserting part 2, the light source device 3 (FIG. 1), the light guide 4 (FIG. 1), an imaging device 5 for an endoscope, a first transmission cable 6, a display device 7, a second transmission cable 8, a control device 9, and a third transmission cable 10 (FIG.

The inserting part 2 has a function as an endoscope according to the present disclosure. In the first embodiment, the inserting part 2 is constituted of a rigid endoscope. That is, the inserting part 2 is rigid or at least part thereof is soft, has a long and narrow shape, and is inserted into the living body. In the inserting part 2, arranged is an optical system configured by using one or a plurality of lenses for condensing light of a subject image.

One end of the light guide 4 is connected to the light source device 3, and the light source device 3 supplies light for illuminating the inside of the living body to the one end of the light guide 4 under control by the control device 9.

One end of the light guide 4 is detachably connected to the light source device 3, and the other end thereof is detachably connected to the inserting part 2. The light guide 4 transfers the light supplied from the light source device 3 from the one end to the other end to be supplied to the inserting part 2. The light supplied to the inserting part 2 is emitted from a distal end of the inserting part 2, and applied to the inside of the living body. The light applied to the inside of the living body (subject image) is condensed by the optical system inside the inserting part 2.

The imaging device 5 for an endoscope is detachably connected to a base end (eyepiece part 21 (FIG. 1)) of the inserting part 2. The imaging device 5 for an endoscope takes the subject image the light of which is condensed by the inserting part 2 under control by the control device 9, and outputs an imaging signal (image signal) obtained by the imaging. As illustrated in FIG. 2, the imaging device 5 for an endoscope includes a lens unit 51 and an imaging part 52.

The lens unit 51 forms, on an imaging surface of the imaging part 52, the subject image the light of which is condensed by the inserting part 2. The lens unit 51 may be moved in an optical axis direction by a driving motor (not illustrated) arranged in the imaging device 5 for an endoscope to adjust a focal distance and a focus.

The imaging part 52 images the inside of the living body under control by the control device 9. The imaging part 52 is configured by using a sensor chip obtained by integrating an imaging element (not illustrated) with a signal processing part (not illustrated), and the like. The imaging element such as a charge coupled device (CCD) or a complementary metal oxide semiconductor (CMOS) receives the subject image the light of which is condensed by the inserting part 2 and formed as the subject image by the lens unit 51, and converts the subject image into an electric signal. The signal processing part performs signal processing (A/D conversion and the like) on the electric signal (analog signal) from the imaging element, and outputs the image signal. The imaging part 52 outputs the image signal (digital signal) after A/D conversion. The signal processing part described above may be separately arranged without being formed integrally with the imaging element.

One end of the first transmission cable 6 is detachably connected to the control device 9 via a connector CN1 (FIG. 1), and the other end thereof is connected to the imaging device 5 for an endoscope via a connector CN2 (FIG. 1). The first transmission cable 6 transmits the image signal output from the imaging device 5 for an endoscope to the control device 9, and transmits, to the imaging device 5 for an endoscope, a control signal, a synchronizing signal, a clock, electric power, and the like output from the control device 9.

In the transmission of the image signal from the imaging device 5 for an endoscope to the control device 9 via the first transmission cable 6, the image signal may be transmitted as an optical signal, or may be transmitted as an electric signal. The same applies to transmission of the control signal, the synchronizing signal, and the clock from the control device 9 to the imaging device 5 for an endoscope via the first transmission cable 6.

Figure 3A:
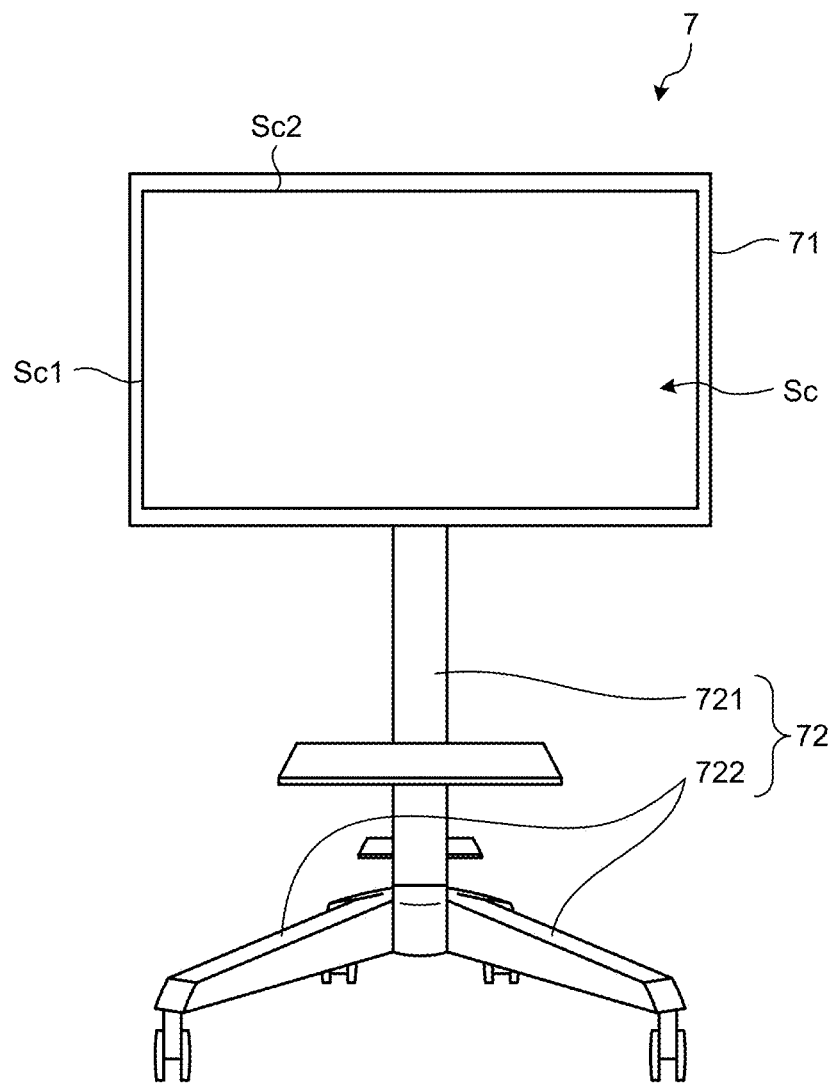
FIG. 3A is a diagram illustrating a display device.
Figure 3B:
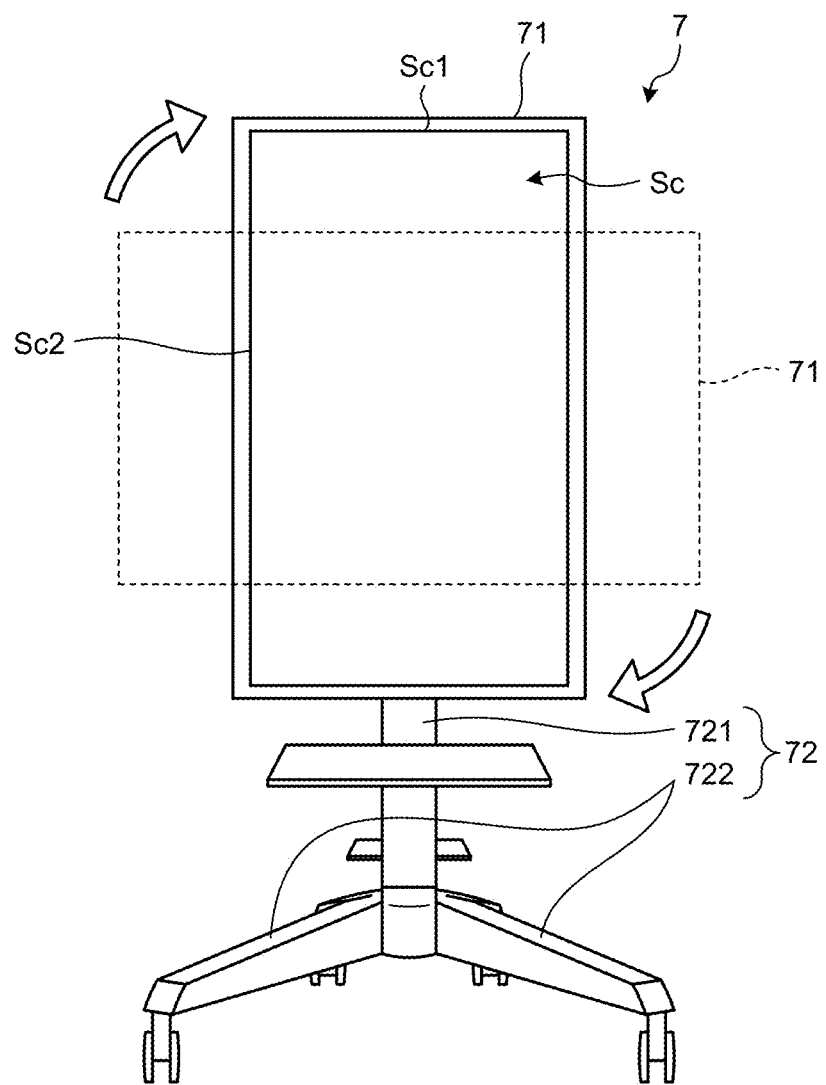
FIG. 3B is a diagram illustrating the display device.

FIGS. 3A and 3B are diagrams illustrating the display device 7.

The display device 7 displays an observation image based on a video signal processed by the control device 9. As illustrated in FIG. 2, FIG. 3A, or FIG. 3B, the display device 7 includes an image display part 71, a support base 72 (FIG. 3A, FIG. 3B), and a state detection part 73 (FIG. 2).

The image display part 71 is configured of a display using liquid crystals, organic electro luminescence (EL), and the like, and displays the observation image on a display screen Sc (FIG. 3A, FIG. 3B). In the first embodiment, the display screen Sc is configured to have a screen size of 40 inches or more. An aspect ratio of the display screen Sc (a ratio between a length dimension of a second side Sc2 (hereinafter, referred to as a long side Sc2) and a length dimension of a first side Sc1 (hereinafter, referred to as a short side Sc1)) is, for example, 16:9.

The support base 72 is a portion for supporting the image display part 71, and includes a pillar 721 and a plurality of leg parts 722 as illustrated in FIG. 3A or FIG. 3B.

The pillar 721 is configured of a pillar-shaped member along a vertical direction, and an upper end thereof is connected to a substantially center position of a back surface of the image display part 71. The pillar 721 supports the image display part 71 in a rotatable manner. Specifically, the pillar 721 supports the image display part 71 so that the image display part 71 may be rotated (set) to be both in a first setting state in which the short side Sc1 of the display screen Sc is along the vertical direction (FIG. 3A (hereinafter, referred to as a horizontal arrangement state)), and in a second setting state in which the long side Sc2 is along the vertical direction (FIG. 3B (hereinafter, referred to as a vertical arrangement state)).

The setting state of the image display part 71 may be manually changed, or the setting state of the image display part 71 may be changed by arranging a motor, a foot switch, and the like so that the motor is driven in accordance with an operation on the foot switch.

Each of the leg parts 722 is a portion that extends from a lower end of the pillar 721 in a direction substantially orthogonal to the pillar 721, and comes into contact with a floor face.

The state detection part 73 detects the setting state (the horizontal arrangement state or the vertical arrangement state) of the image display part 71, and outputs a detection signal corresponding to the detection result. Examples of the state detection part 73 include a gravity sensor, an orientation sensor, an acceleration sensor, or an encoder and a rotation angle detection switch arranged at a connecting portion between the pillar 721 and the image display part 71.

One end of the second transmission cable 8 is detachably connected to the display device 7, and the other end thereof is detachably connected to the control device 9. The second transmission cable 8 transmits the video signal processed by the control device 9 to the display device 7, and transmits a detection signal related to the setting state (the horizontal arrangement state or the vertical arrangement state) of the image display part 71 to the control device 9.

The control device 9 includes a central processing unit (CPU) and the like, and centrally controls operations of the light source device 3, the imaging device 5 for an endoscope, and the display device 7 via the first to third transmission cables 6, 8, and 10 in accordance with a computer program (including an image processing program) recorded in a memory (not illustrated). As illustrated in FIG. 2, the control device 9 includes an image acquisition part 91 and an image processing device 92 for an endoscope. That is, in the first embodiment, the image processing device 92 for an endoscope according to the present disclosure is arranged in the control device 9.

The image acquisition part 91 causes the imaging device 5 for an endoscope (imaging part 52) to take the subject image, and acquires an image signal (taken image) from the imaging part 52. The image acquisition part 91 then outputs the acquired taken image to the image processing device 92 for an endoscope.

By performing predetermined processing on the taken image acquired from the imaging device 5 for an endoscope, the image processing device 92 for an endoscope generates and outputs a video signal corresponding to the setting state (the horizontal arrangement state or the vertical arrangement state) of the image display part 71.

Detailed configuration of the image processing device 92 for an endoscope will be described later.

One end of the third transmission cable 10 is detachably connected to the light source device 3, and the other end thereof is detachably connected to the control device 9. The third transmission cable 10 transmits a control signal from the control device 9 to the light source device 3.

Configuration of Image Processing Device for Endoscope

Next, the following describes a configuration of the image processing device 92 for an endoscope with reference to FIG. 2.

As illustrated in FIG. 2, the image processing device 92 for an endoscope includes a setting state recognition part 921, a subject image discriminating part 922, a magnification setting part 923, and a video signal generation part 924.

The setting state recognition part 921 recognizes the setting state (the horizontal arrangement state or the vertical arrangement state) of the image display part 71 based on the detection signal input from the display device 7 (state detection part 73) via the second transmission cable 8.

Figure 4:
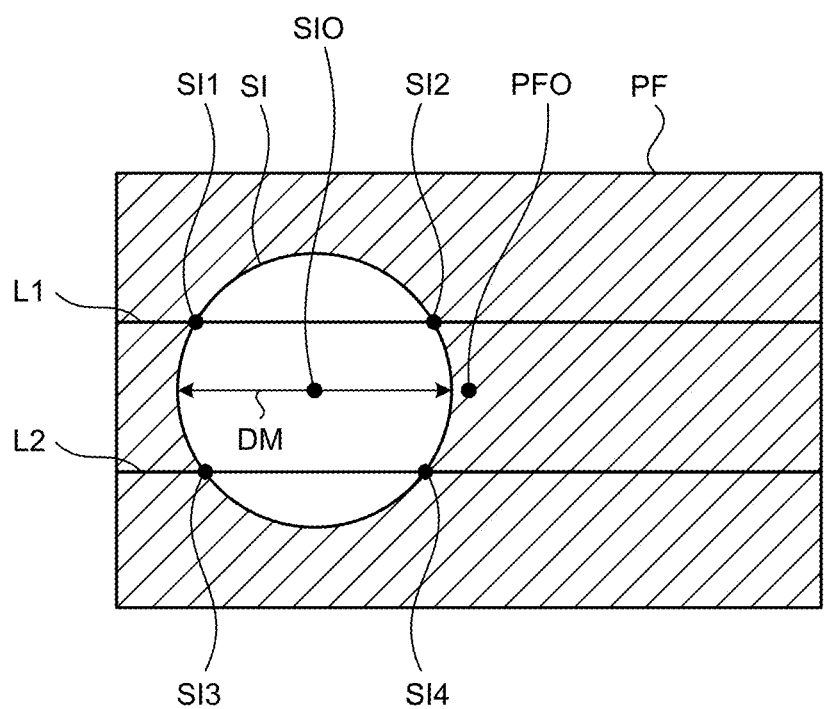
FIG. 4 is a diagram for explaining a function of a subject image discriminating part.
Figure 5A:
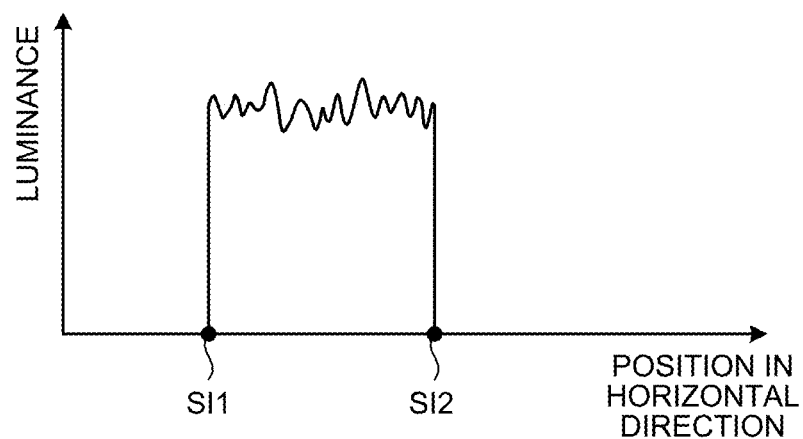
FIG. 5A is a diagram for explaining a function of the subject image discriminating part.
Figure 5B:
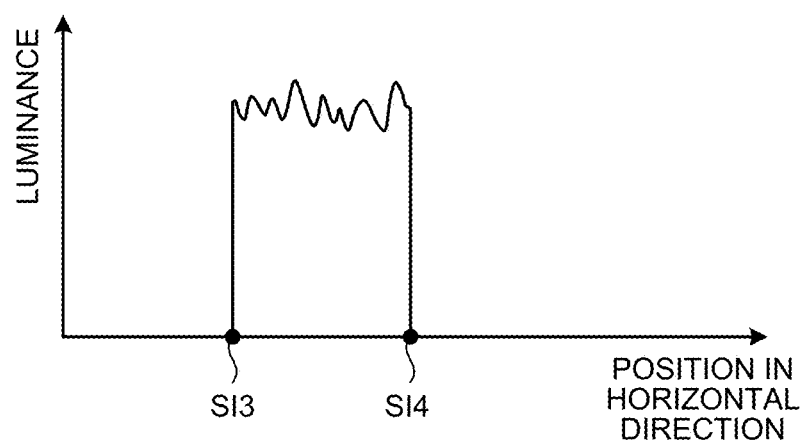
FIG. 5B is a diagram for explaining a function of the subject image discriminating part.

FIGS. 4, 5A, and 5B are diagrams for explaining a function of the subject image discriminating part 922. Specifically, FIG. 4 is a diagram illustrating an example of a taken image PF taken by the imaging part 52. FIG. 5A is a diagram illustrating luminance distribution on a horizontal line L1 in the taken image PF illustrated in FIG. 4. FIG. 5B is a diagram illustrating luminance distribution on a horizontal line L2 in the taken image PF illustrated in FIG. 4.

The subject image discriminating part 922 discriminates a subject image SI (FIG. 4) in the taken image PF (for example, a position SIO (FIG. 4) and a size of the subject image SI) based on the taken image PF (FIG. 4) acquired by the image acquisition part 91.

The subject image SI in the taken image PF taken by the imaging part 52 has a substantially circular shape, as illustrated in FIG. 4. Thus, the subject image discriminating part 922 discriminates a diameter DM (FIG. 4) of the subject image SI as the size of the subject image SI in the taken image PF.

Specifically, as illustrated in FIG. 4, the subject image discriminating part 922 detects luminance distribution on a plurality of (in the first embodiment, two) horizontal lines L1 and L2 in the taken image PF. In the taken image PF, a region of the subject image SI is brighter than the other region (in FIG. 4, a hatched region (blank region)). That is, as illustrated in FIG. 5A, regarding the luminance distribution on the horizontal line L1, luminance is high between two intersection points SI1 and SI2 intersecting with a boundary of the subject image SI, and the luminance is low in other portions. Similarly, regarding the luminance distribution on the horizontal line L2, as illustrated in FIG. 5B, the luminance is high between two intersection points SI3 and SI4 intersecting with the boundary of the subject image SI, and the luminance is low in other portions. Thus, by detecting the luminance distribution on the horizontal lines L1 and L2, the subject image discriminating part 922 may recognize the intersection points SI1 to SI4 intersecting with the boundary of the subject image SI. By calculating a curvature center of the intersection points SI1 to SI4, the subject image discriminating part 922 discriminates (calculates) a center position SIO of the subject image SI in the taken image PF. By calculating a distance between the center position SIO and any of the intersection points SI1 to SI4, the subject image discriminating part 922 discriminates (calculates) the diameter DM of the subject image SI in the taken image PF.

The magnification setting part 923 sets magnification/reduction ratio of the subject image SI based on a recognition result obtained by the setting state recognition part 921 and a discrimination result obtained by the subject image discriminating part 922.

Specifically, when the image display part 71 is set in the horizontal arrangement state, the magnification setting part

923 sets the magnification/reduction ratio of the subject image SI to be a default value (for example, "1 (a value for not performing magnification or reduction)"). In a case in which the diameter DM of the subject image SI in the taken image PF is equal to or smaller than a threshold (hereinafter, referred to as a reference threshold) corresponding to the length dimension of the short side Sc1 of the display screen Sc and the image display part 71 is set in the vertical arrangement state, the magnification setting part 923 sets the magnification/reduction ratio of the subject image SI to be the same value (the default value (for example, "1")) as that in a case in which the image display part 71 is set in the horizontal arrangement state. On the other hand, in a case in which the diameter DM of the subject image SI in the taken image PF is larger than the reference threshold and the image display part 71 is set in the vertical arrangement state, the magnification setting part 923 sets the magnification/reduction ratio of the subject image SI to be a value smaller than the default value (for example, "9/16 (a value corresponding to the aspect ratio (16:9) of the taken image PF)").

The video signal generation part 924 performs various pieces of image processing on the taken image PF acquired by the image acquisition part 91. Examples of the image processing include magnification/reduction adjustment, eccentricity correction, rotation correction, and position movement correction of the subject image SI in addition to known image processing such as gain adjustment, white balance adjustment, gamma correction, and contour emphasis correction.

The magnification/reduction adjustment of the subject image SI described above is performed as follows.

The video signal generation part 924 performs magnification/reduction adjustment on the subject image SI discriminated by the subject image discriminating part 922 based on the magnification/reduction ratio set by the magnification setting part 923.

The eccentricity correction of the subject image SI described above is performed as follows.

The subject image, which is obtained when light is applied to the inside of the living body and reflected from the living body, is imaged by the imaging part 52 via an objective optical system (not illustrated) arranged at a distal end of the inserting part 2, an image transmission optical system (not illustrated) arranged in the inserting part 2 for transmitting the subject image from the objective optical system to the eyepiece part 21, an eyepiece optical system (not illustrated) arranged in the eyepiece part 21, and the lens unit 51. In this case, optical axes of the objective optical system, the image transmission optical system, the eyepiece optical system, and the lens unit 51 deviate from each other, for example, the center position SIO of the subject image SI may deviate from (become eccentric to) a center position PFO of the taken image PF as illustrated in FIG. 4. In this way, when the subject image SI is eccentric, the subject image SI is also eccentric in the display screen Sc (the center position SIO deviates from the center position of the display screen Sc).

The video signal generation part 924 performs processing (eccentricity correction of the subject image SI) of moving the subject image SI discriminated by the subject image discriminating part 922, and causing the center position SIO of the subject image SI to be matched with the center position PFO of the taken image PF (matched with the center position of the display screen Sc).

The rotation correction of the subject image SI described above is performed as follows.

When the image display part 71 is set in the horizontal arrangement state or the vertical arrangement state, an up-and-down direction of the subject image SI needs to be adjusted to be along a vertical direction in accordance with the setting state of the image display part 71.

When the setting state recognition part 921 recognizes that the image display part 71 is set in the vertical arrangement state, the video signal generation part 924 performs processing (rotation correction of the subject image SI) of rotating the subject image SI discriminated by the subject image discriminating part 922 by 90° so that an orientation of the subject image SI is caused to correspond to the vertical arrangement state of the image display part 71 (the up-and-down direction of the subject image SI is caused to be along the vertical direction).

The up-and-down direction of the subject image SI is set to be along the vertical direction (an extending direction of the short side Sc1) without performing the rotation correction described above when the image display part 71 is set in the horizontal arrangement state. Thus, when the setting state recognition part 921 recognizes that the image display part 71 is set in the horizontal arrangement state, the video signal generation part 924 does not perform rotation correction on the subject image SI.

The position movement correction of the subject image SI described above is performed as follows.

When the setting state recognition part 921 recognizes that the image display part 71 is set in the vertical arrangement state, the video signal generation part 924 performs the rotation correction described above, and performs processing (position movement correction of the subject image SI) of positioning the subject image SI discriminated by the subject image discriminating part 922 in a region corresponding to an upper region of the display screen Sc of the image display part 71 set in the vertical arrangement state in the taken image PF after the rotation correction.

The video signal generation part 924 then generates a video signal corresponding to the taken image PF after the image processing described above, and outputs the video signal to the image display part 71 via the second transmission cable 8.

Operation of Image Processing Device for Endoscope

Next, the following describes an operation (image processing method) of the image processing device 92 for an endoscope described above.

FIG. 6 is a flowchart illustrating an operation of the image processing device 92 for an endoscope.

First, the image acquisition part 91 causes the imaging part 52 to take the subject image SI, and acquires the taken image PF taken by the imaging part 52 (Step S1). The image acquisition part 91 then outputs the acquired taken image PF to the subject image discriminating part 922 and the video signal generation part 924.

Next, the subject image discriminating part 922 discriminates the subject image SI in the taken image PF based on the taken image PF acquired by the image acquisition part 91 (Step S2). Accordingly, the center position SIO and the diameter DM of the subject image SI in the taken image PF is discriminated (calculated).

Next, the video signal generation part 924 determines whether the center position SIO of the subject image SI deviates from the center position PFO of the taken image PF (misregistration is present) (Step S3).

If it is determined that misregistration is present (Yes at Step S3), the video signal generation part 924 performs eccentricity correction on the subject image SI in the taken image PF acquired by the image acquisition part 91 (Step S4).

If it is determined that misregistration is not present (No at Step S3), or after Step S4, the setting state recognition part 921 recognizes the setting state (the horizontal arrangement state or the vertical arrangement state) of the image display part 71 based on a detection signal input from the state detection part 73 via the second transmission cable 8 (Step S5: setting state recognition step).

Next, the setting state recognition part 921 determines whether the image display part 71 is set in the horizontal arrangement state (Step S6).

If it is determined that the image display part 71 is set in the horizontal arrangement state (Yes at Step S6), the magnification setting part 923 sets the magnification/reduction ratio of the subject image SI to be a default value (for example, "1") (Step S7).

After Step S7, the video signal generation part 924 performs magnification/reduction adjustment on the subject image SI based on the magnification/reduction ratio set at Step S7 in the taken image PF on which eccentricity correction (Step S4) is performed or in the taken image PF on which eccentricity correction is not performed (Step S8). After this, the process of the image processing device 92 for an endoscope proceeds to Step S15.

On the other hand, if it is determined that the image display part 71 is set in the vertical arrangement state (No at Step S6), the magnification setting part 923 determines whether the diameter DM of the subject image SI in the taken image PF is larger than the reference threshold (Step S9).

If it is determined that the diameter DM of the subject image SI is larger than the reference threshold (Yes at Step S9), the magnification setting part 923 sets the magnification/reduction ratio of the subject image SI to be a smaller value than the default value (for example, "9/16") (Step S10).

On the other hand, if it is determined that the diameter DM of the subject image SI is equal to or smaller than the reference threshold (No at Step S9), the magnification setting part 923 sets the magnification/reduction ratio of the subject image SI to be a default value (for example, "1") (Step S11).

After Step S10 or S11, the video signal generation part 924 performs magnification/reduction adjustment on the subject image SI based on the magnification/reduction ratio set at Step S10 or S11 in the taken image PF on which eccentricity correction (Step S4) is performed, or in the taken image PF on which eccentricity correction is not performed (Step S12).

After Step S12, the video signal generation part 924 performs rotation correction (Step S13) on the subject image SI, and performs position movement correction (Step S14) on the subject image SI in the taken image PF after magnification/reduction adjustment (Step S12).

After Step S8 or S14, the video signal generation part 924 generates a video signal corresponding to the taken image PF on which the image processing described above is performed, and outputs the video signal to the image display part 71 via the second transmission cable 8 (Step S15).

Steps S13 and S15 described above correspond to a video signal generation step according to the present disclosure.

Regarding various pieces of image processing performed by the video signal generation part 924, timings for performing eccentricity correction (Step S4), magnification/reduction adjustment (Steps S8 and S12), rotation correction (Step S13), and position movement correction (Step S14) on the subject image SI are not limited to the timings illustrated in FIG. 6. The processing may be performed at a different timing. Other pieces of image processing (for example, gain adjustment, white balance adjustment, gamma correction, and contour emphasis correction) may be performed at any timing. That is, each of the other pieces of image processing may be performed at a timing of Step S15, or may be performed at a timing before Step S4.

Specific Example of Display Form

The following describes a specific example of the observation image displayed on the image display part 71 through the operation of the image processing device 92 for an endoscope described above.

The following sequentially describes a display form in a case in which the inserting part 2 is an endoscope having a small diameter, and a display form in a case in which the inserting part 2 is an endoscope having a large diameter.

Figure 7A:
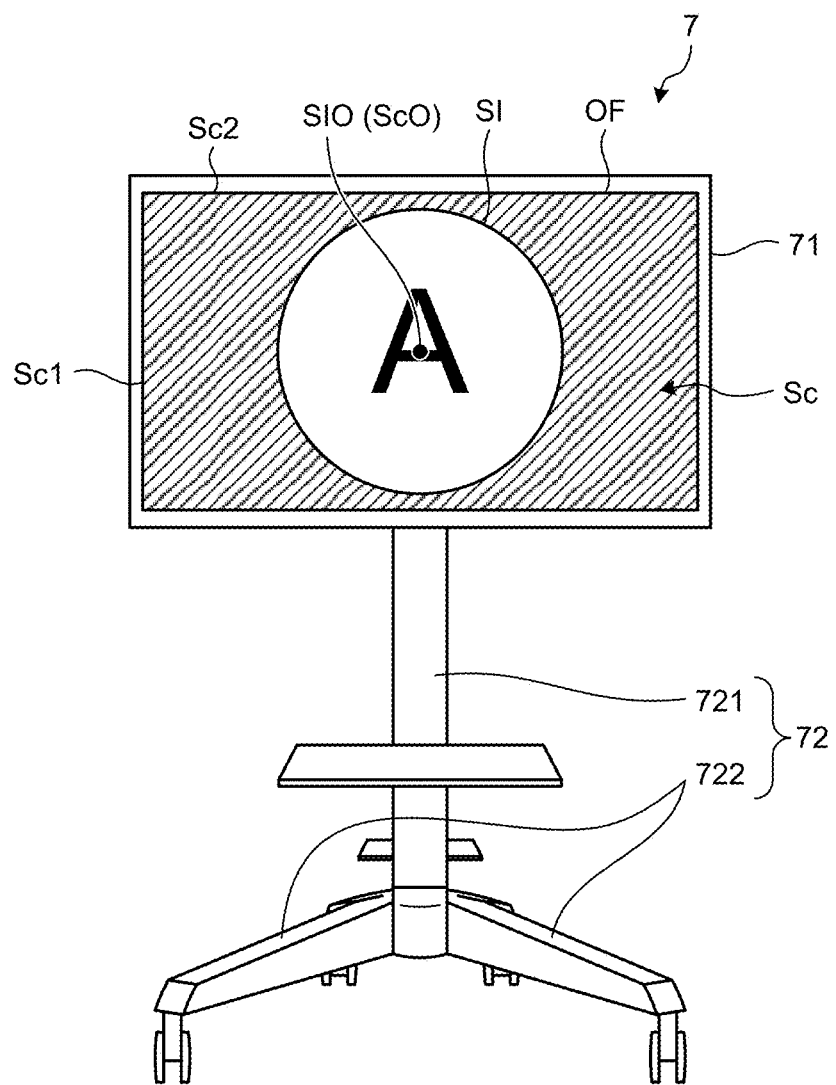
FIG. 7A is a diagram illustrating an example of an observation image that is displayed on an image display part through an operation of the image processing device for an endoscope when an inserting part is an endoscope having a small diameter.
Figure 7B:
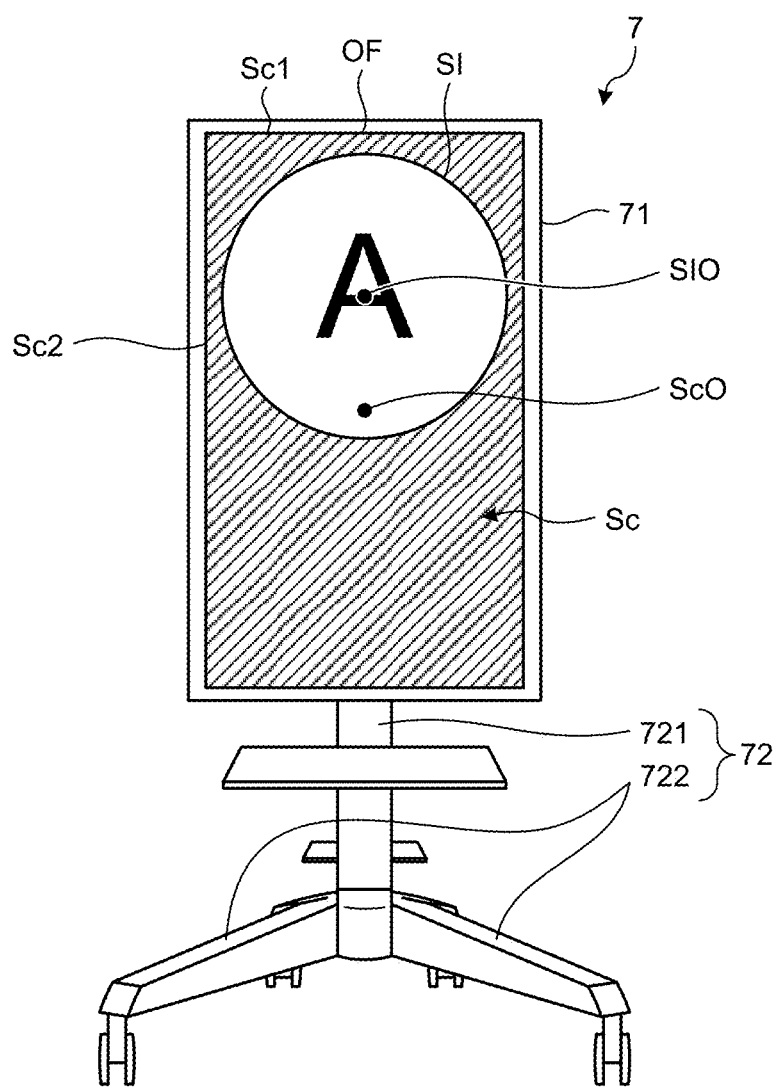
FIG. 7B is a diagram illustrating an example of the observation image that is displayed on the image display part through an operation of the image processing device for an endoscope when the inserting part is an endoscope having a small diameter.

Display Form in Case in which Inserting Part is Endoscope Having a Small Diameter FIGS. 7A and 7B are diagrams illustrating an example of an observation image OF that is displayed on the image display part 71 through the operation of the image processing device 92 for an endoscope when the inserting part 2 is an endoscope having a small diameter. In FIGS. 7A and 7B, a character "A" is described in the subject image SI for convenience to clarify the up-and-down direction of the subject image SI.

When the inserting part 2 is an endoscope having a small diameter, the subject image SI captured by the inserting part 2 has a small diameter (the diameter DM is equal to or smaller than the reference threshold (No at Step S9)). Thus, the whole subject image SI is positioned within the image region without extending off the image region of the taken image PF.

If the image display part 71 is set in the horizontal arrangement state (Yes at Step S6), the video signal explained below is generated and output (Step S15).

That is, the video signal is obtained when the eccentricity correction (Step S4) is performed on the subject image SI in accordance with the misregistration (Yes at Step S3) of the subject image SI, and the rotation correction (Step S13) is not performed on the subject image SI.

Thus, the observation image OF illustrated in FIG. 7A is displayed on the image display part 71 set in the horizontal arrangement state based on the video signal.

That is, in the observation image OF, the center position SIO of the subject image SI is positioned at a center position ScO of the display screen Sc, and the whole subject image SI having a circular shape is positioned within the display screen Sc. In the observation image OF, the subject image SI has an orientation such that the up-and-down direction thereof is along the short side Sc1 (vertical direction).

On the other hand, if the image display part 71 is set in the vertical arrangement state (No at Step S6), the video signal explained below is generated and output (Step S15).

That is, the video signal is obtained when the eccentricity correction (Step S4) is performed on the subject image SI in accordance with the misregistration (Yes at Step S3) of the subject image SI, and the rotation correction (Step S13) and the position movement correction (Step S14) are performed on the subject image SI. The video signal is obtained when the magnification/reduction adjustment (Step S12) is performed on the subject image SI at the same magnification/reduction ratio (default value (for example, "1")) as that in a case in which the image display part 71 is set in the horizontal arrangement state.

Thus, the observation image OF illustrated in FIG. 7B is displayed on the image display part 71 set in the vertical arrangement state based on the video signal.

That is, in the observation image OF, the whole subject image SI having a circular shape is positioned within the display screen Sc, and the center position SIO of the subject image SI is positioned in an upper region of the display screen Sc. In the observation image OF, the subject image SI has an orientation such that the up-and-down direction thereof is along the long side Sc2 (vertical direction). In the observation image OF, the size of the subject image SI is the same as the size of the subject image SI in a case in which the image display part 71 is set in the horizontal arrangement state.

Display Form in Case in which Inserting Part is Endoscope Having Large Diameter

Figure 8A:
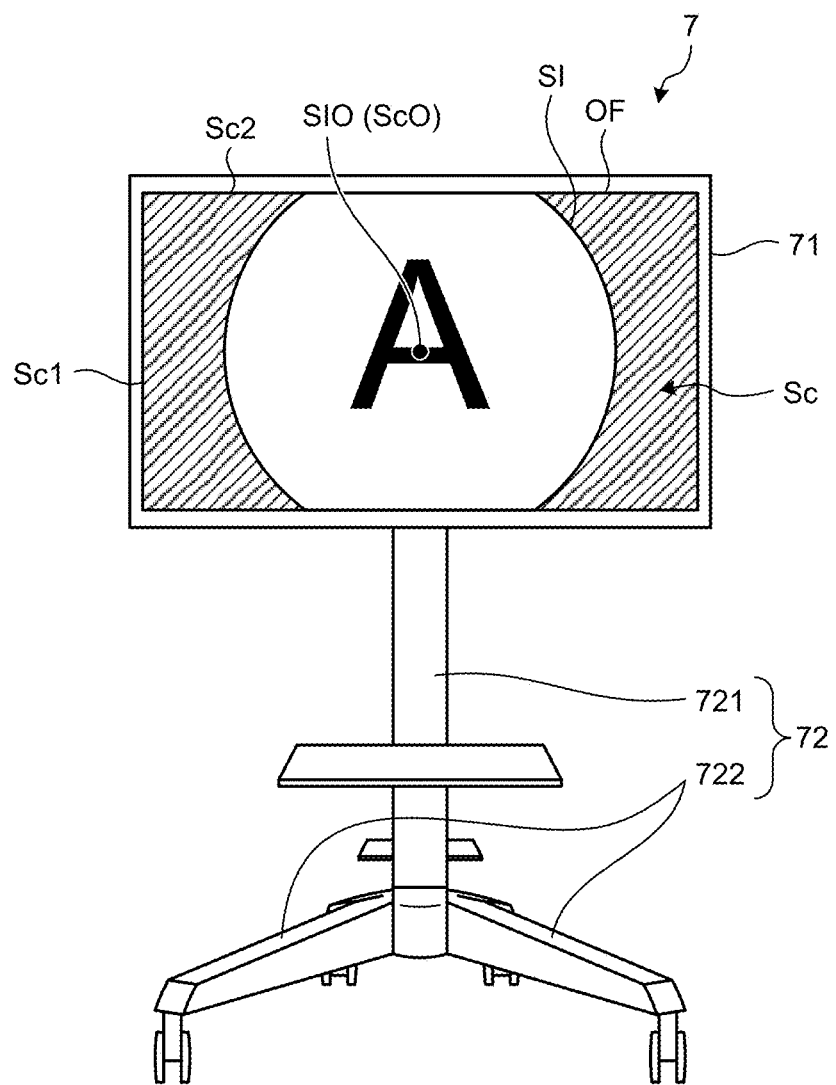
FIG. 8A is a diagram illustrating an example of the observation image that is displayed on the image display part through an operation of the image processing device for an endoscope when the inserting part is an endoscope having a large diameter.
Figure 8B:
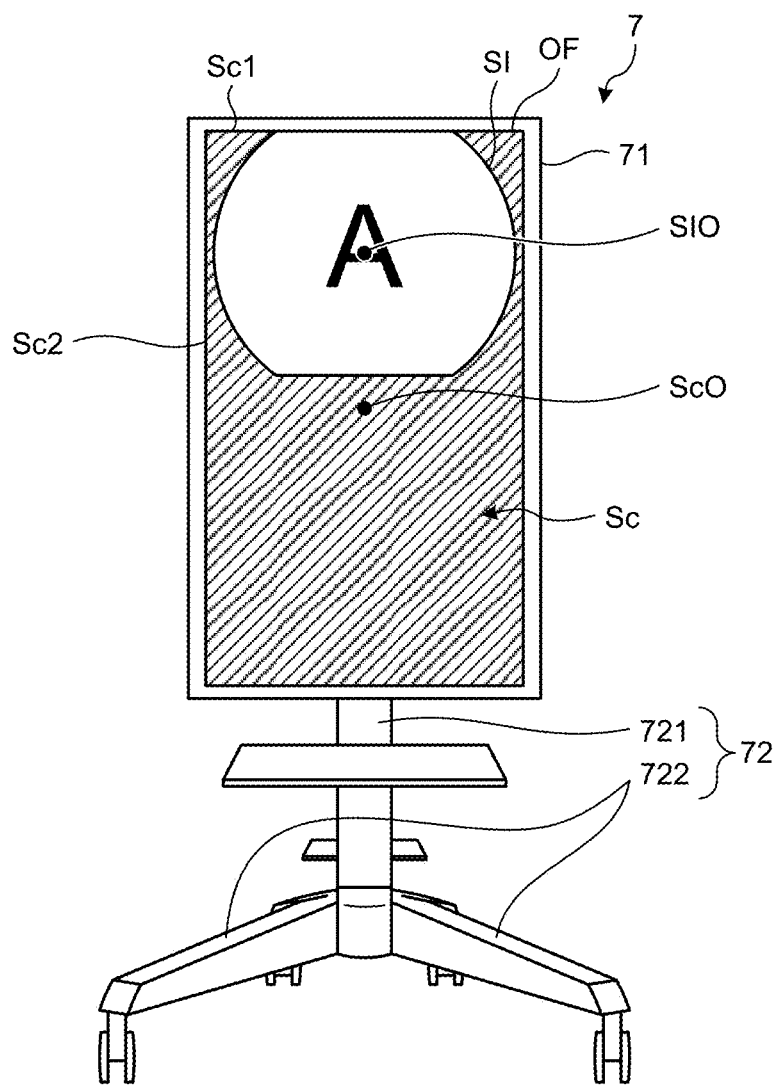
FIG. 8B is a diagram illustrating an example of the observation image that is displayed on the image display part through an operation of the image processing device for an endoscope when the inserting part is an endoscope having a large diameter.

FIGS. 8A and 8B are diagrams illustrating an example of the observation image OF that is displayed on the image display part 71 through the operation of the image processing device 92 for an endoscope when the inserting part 2 is an endoscope having a large diameter. In FIGS. 8A and 8B, similarly to FIGS. 7A and 7B, the character "A" is described in the subject image SI for convenience to clarify the up-and-down direction of the subject image SI.

When the inserting part 2 is an endoscope having a large diameter, the subject image SI captured by the inserting part 2 has a large diameter (the diameter DM is larger than the reference threshold (Yes at Step S9)). Thus, upper and lower portions of the circular subject image SI extend off the image region of the taken image PF.

If the image display part 71 is set in the horizontal arrangement state (Yes at Step S6), the video signal explained below is generated and output (Step S15).

That is, the video signal is obtained when the eccentricity correction (Step S4) is performed on the subject image SI in accordance with the misregistration (Yes at Step S3) of the subject image SI, and the rotation correction (Step S13) is not performed on the subject image SI.

Thus, the observation image OF illustrated in FIG. 8A is displayed on the image display part 71 set in the horizontal arrangement state based on the video signal.

That is, in the observation image OF, the whole circular subject image SI the upper and lower portions of which are cut is positioned within the display screen Sc, and the center position SIO of the subject image SI is positioned at the center position ScO of the display screen Sc. In the observation image OF, the subject image SI has an orientation such that the up-and-down direction thereof is along the short side Sc1 (vertical direction).

On the other hand, if the image display part 71 is set in the vertical arrangement state (No at Step S6), the video signal explained below is generated and output (Step S15).

That is, the video signal is obtained when the eccentricity correction (Step S4) is performed on the subject image SI in accordance with the misregistration (Yes at Step S3) of the subject image SI, and the rotation correction (Step S13) and the position movement correction (Step S14) are performed on the subject image SI. The video signal is obtained when the magnification/reduction adjustment (Step S12) is performed on the subject image SI at the magnification/reduction ratio (for example, "9/16") smaller than that in a case in which the image display part 71 is set in the horizontal arrangement state.

Thus, the observation image OF illustrated in FIG. 8B is displayed on the image display part 71 set in the vertical arrangement state based on the video signal.

That is, in the observation image OF, the whole circular subject image SI the upper and lower portions of which are cut is positioned within the display screen Sc, and the center position SIO of the subject image SI is positioned in an upper region of the display screen Sc. In the observation image OF, the subject image SI has an orientation such that the up-and-down direction thereof is along the long side Sc2 (vertical direction). Additionally, in the observation image OF, the size of the subject image SI is smaller than the size of the subject image SI in a case in which the image display part 71 is set in the horizontal arrangement state.

For example, at Step S10, when the magnification/reduction ratio of the subject image SI is set to be the same as the magnification/reduction ratio (a default value (for example, "1")) in a case in which the image display part 71 is set in the horizontal arrangement state, the whole circular subject image SI the upper and lower portions of which are cut is not fit within the display screen Sc (the left and right portions of the subject image SI extend off the display screen Sc).

In the first embodiment, Step S9 is performed to cause the whole circular subject image SI the upper and lower portions of which are cut to be fit within the display screen Sc, and if the diameter DM is larger than the reference threshold (Yes at Step S9), the magnification/reduction ratio of the subject image SI is set to be smaller than the default value (Step S10). That is, the subject image SI is reduced as compared with the subject image SI in a case in which the image display part 71 is set in the horizontal arrangement state (Step S12).

The image processing device 92 for an endoscope according to the first embodiment described above processes the taken image PF including the subject image SI captured by the inserting part 2 to generate the video signal, and outputs the video signal to the image display part 71. The image display part 71 then displays the observation image OF based on the video signal. The image display part 71 is configured to be able to be set in the horizontal arrangement state or the vertical arrangement state. The image processing device 92 for an endoscope recognizes the setting state (the horizontal arrangement state or the vertical arrangement state) of the image display part 71, and generates the video signal so that the subject image SI in the observation image OF has an orientation corresponding to the setting state of the image display part 71.

That is, the setting state of the image display part 71 is changed from the horizontal arrangement state to the vertical arrangement state, the width of the display screen Sc is reduced because the short side Sc1 is along the horizontal direction, so that the path of flow may be secured for a person standing in the vicinity of the image display part 71. Even if the setting state of the image display part 71 is changed from the horizontal arrangement state to the vertical arrangement state, the subject image SI in the observation image OF has an orientation corresponding to the setting state of the image display part 71 (the up-and-down direction of the subject image SI is along the vertical direction). Thus, after the path of flow is secured for the person standing in the vicinity of the image display part 71, there is no need to change the setting state of the image display part 71 again from the vertical arrangement state to the horizontal arrangement state.

Accordingly, with the image processing device 92 for an endoscope according to the first embodiment, cumbersome work of moving the setting place of the image display part 71 is not required, so that convenience may be improved.

In the image processing device 92 for an endoscope according to the first embodiment, when the diameter DM of the subject image SI in the taken image PF is equal to or smaller than the reference threshold, the magnification/reduction ratio of the subject image SI in the horizontal arrangement state is the same as the magnification/reduction ratio of the subject image SI in the vertical arrangement state.

Accordingly, for example, in a case of observing the subject image SI captured by the inserting part 2 configured of an endoscope having a small diameter, the size of the subject image SI does not have to be unnecessarily reduced when the setting state of the image display part 71 is changed from the horizontal arrangement state to the vertical arrangement state, and the subject image SI may be observed in the same size in both the horizontal arrangement state and the vertical arrangement state.

In the image processing device 92 for an endoscope according to the first embodiment, when the diameter DM of the subject image SI in the taken image PF is larger than the reference threshold, the magnification/reduction ratio of the subject image SI in the vertical arrangement state is smaller than the magnification/reduction ratio of the subject image SI in the horizontal arrangement state. That is, only in a case in which the setting state of the image display part 71 is changed from the horizontal arrangement state to the vertical arrangement state, and it is determined that the subject image SI is not fit within the display screen Sc, the size of the subject image SI in the vertical arrangement state is reduced as compared with the subject image SI in the horizontal arrangement state.

Thus, for example, in a case of observing the subject image SI captured by the inserting part 2 configured of an endoscope having a large diameter, the whole subject image SI may be observed when the setting state of the image display part 71 is changed from the horizontal arrangement state to the vertical arrangement state.

The image processing device 92 for an endoscope according to the first embodiment generates the video signal obtained by performing eccentricity correction and position movement correction on the subject image SI.

Thus, when the image display part 71 is set in the horizontal arrangement state, the subject image SI is positioned in a center region of the display screen Sc. On the other hand, when the image display part 71 is set in the vertical arrangement state, the subject image SI is positioned in an upper region of the display screen Sc. Accordingly, the image display part 71 may display the subject image SI such that it is easily observed in both the horizontal and the vertical arrangement states.

Second Embodiment

Next, the following describes a second embodiment of the present disclosure.

In the following description, the same component as that in the first embodiment described above is denoted by the same reference numeral, and detailed description thereof will not be repeated or is simplified.

Figure 9:
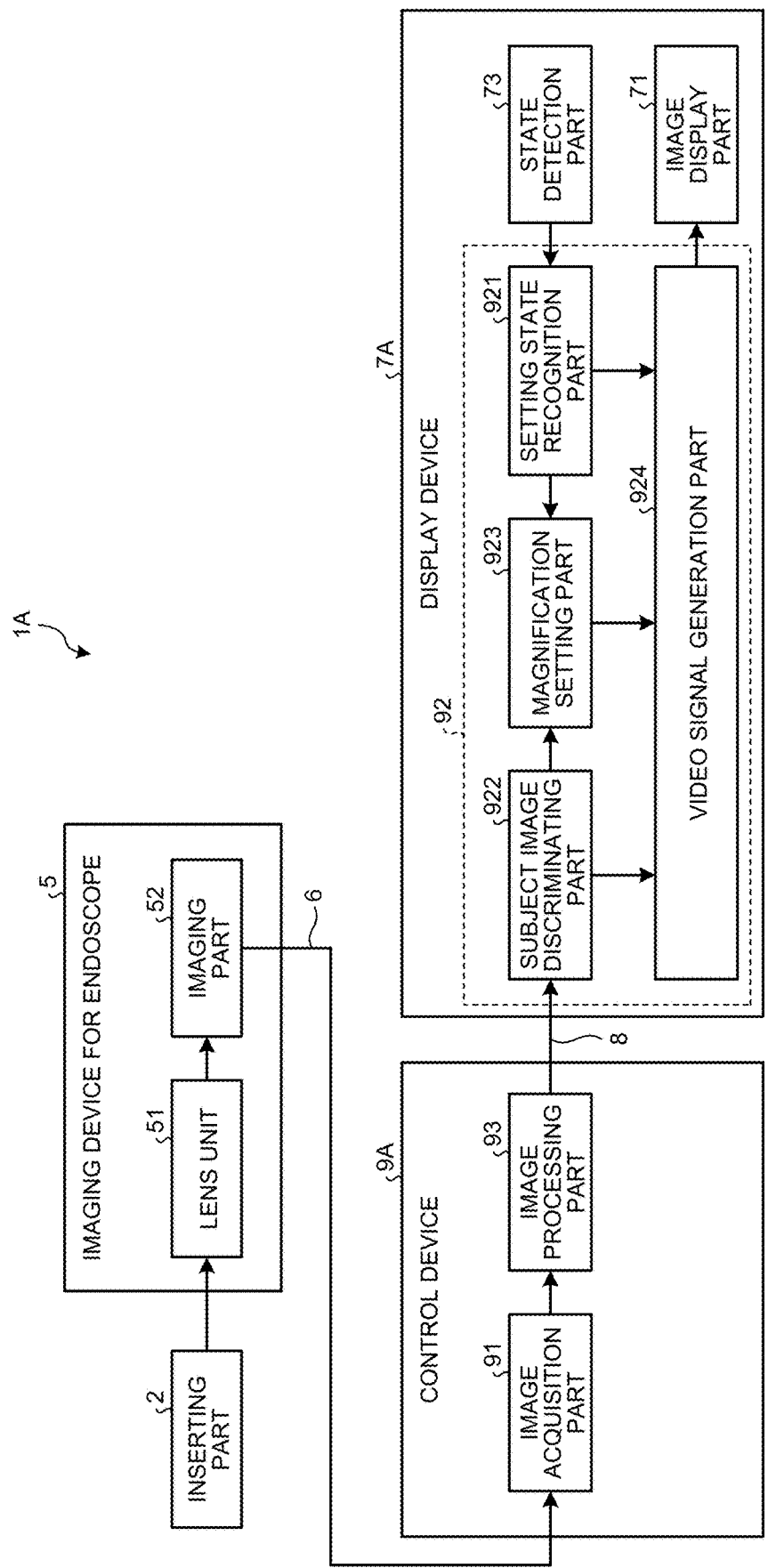
FIG. 9 is a block diagram illustrating a configuration of an endoscope device according to a second embodiment of the present disclosure.

FIG. 9 is a block diagram illustrating a configuration of an endoscope device 1A according to the second embodiment of the present disclosure. Similarly to FIG. 2, for convenience of explanation, FIG. 9 does not illustrate the light source device 3, the light guide 4, and the third transmission cable 10.

In the endoscope device 1 according to the first embodiment described above, the image processing device 92 for an endoscope is arranged in the control device 9.

In contrast, in the endoscope device 1A according to the second embodiment, as illustrated in FIG. 9, a control device 9A not including the image processing device 92 for an endoscope is used in place of the control device 9, and a display device 7A including the image processing device 92 for an endoscope mounted thereon is used in place of the display device 7.

As illustrated in FIG. 9, the control device 9A includes an image processing part 93 in place of the omitted image processing device 92 for an endoscope.

The image processing part 93 performs various pieces of image processing on the taken image PF acquired by the image acquisition part 91. Examples of the image processing include known image processing such as gain adjustment, white balance adjustment, gamma correction, and contour emphasis correction. The image processing part 93 then outputs a signal corresponding to the taken image PF after the image processing to the display device 7A (image processing device 92 for an endoscope) via the second transmission cable 8.

The image processing device 92 for an endoscope mounted on the display device 7A performs processing similar to the processing explained in the first embodiment (excluding the image processing performed by the image processing part 93 described above) on the signal output from the control device 9A.

Even when the image processing device 92 for an endoscope is arranged in the display device 7A as described in the second embodiment, the same effect as that in the first embodiment described above may be obtained.

OTHER EMBODIMENTS

The modes for carrying out the present disclosure have been described above. However, the present disclosure is not limited to the first and the second embodiments described above.

In the first and the second embodiments, the image processing device 92 for an endoscope according to the present disclosure is mounted on the control device 9 or the display device 7A, but the embodiment is not limited thereto. For example, the image processing device 92 for an endoscope according to the present disclosure may be constituted of a module separate from the control device and the display device, and arranged in a signal transmission path between the control device and the display device.

In the first and the second embodiments described above, the inserting part 2 constituted of a rigid endoscope is used as the endoscope according to the present disclosure, but the embodiment is not limited thereto. The inserting part 2 may be constituted of a soft endoscope so long as the endoscope includes an eyepiece part.

Figure 10A:
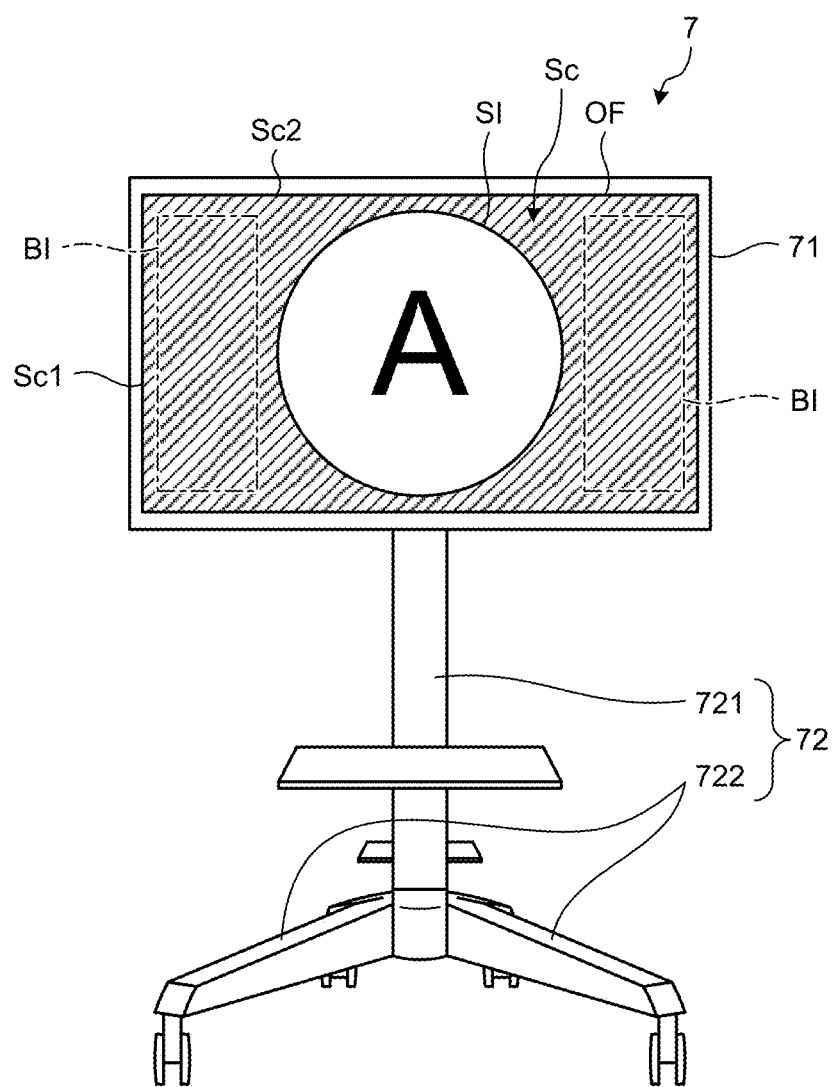
FIG. 10A is a diagram illustrating a modification of the first and second embodiments of the present disclosure.
Figure 10B:
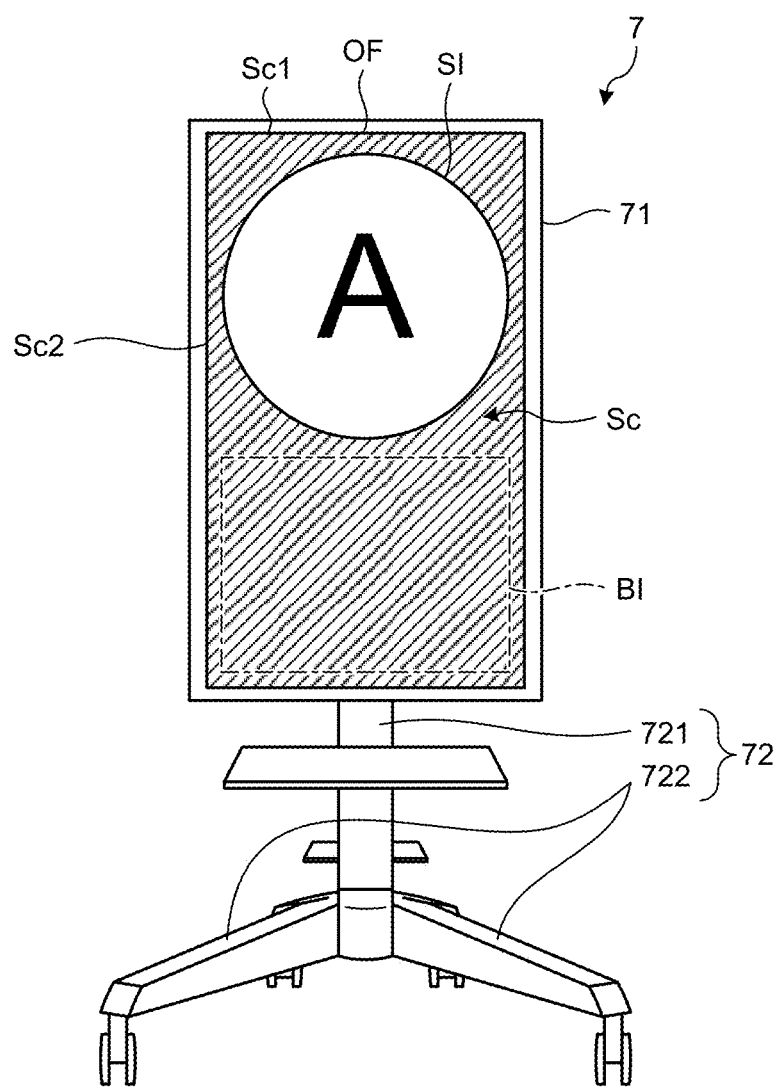
FIG. 10B is a diagram illustrating a modification of the first and second embodiments of the present disclosure.

FIGS. 10A and 10B are diagrams illustrating a modification of the first and the second embodiments of the present disclosure. Specifically, FIGS. 10A and 10B correspond to FIGS. 7A and 7B, respectively.

In the first and the second embodiments, as illustrated in FIG. 10A or FIG. 10B, various pieces of information (for example, subject information (for example, an ID, a date of birth, and a name), identification information of the inserting part 2 (for example, an ID and an examination corresponding item), and examination content) may be displayed in a region BI excluding the subject image SI in the observation image OF.

Figure 11A:
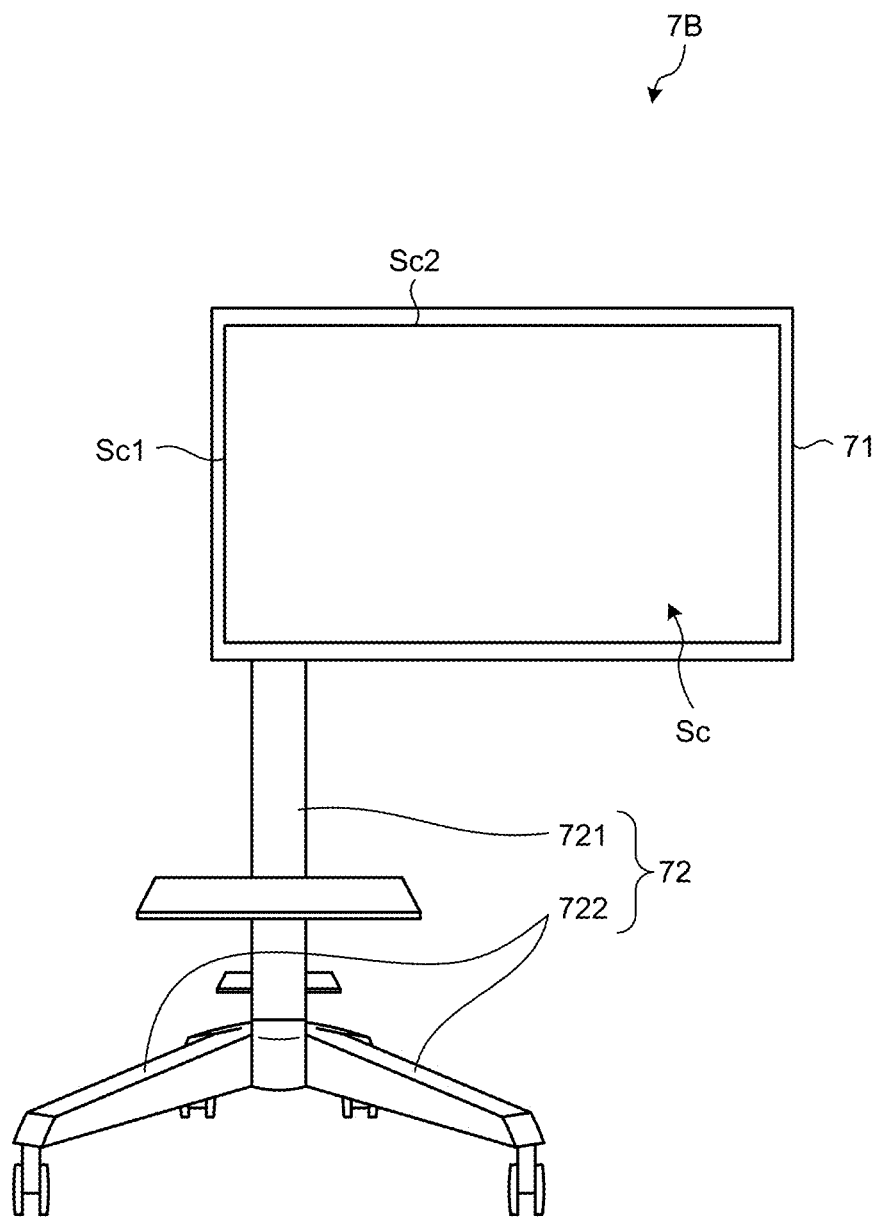
FIG. 11A is a diagram illustrating a modification of the first and second embodiments of the present disclosure.
Figure 11B:
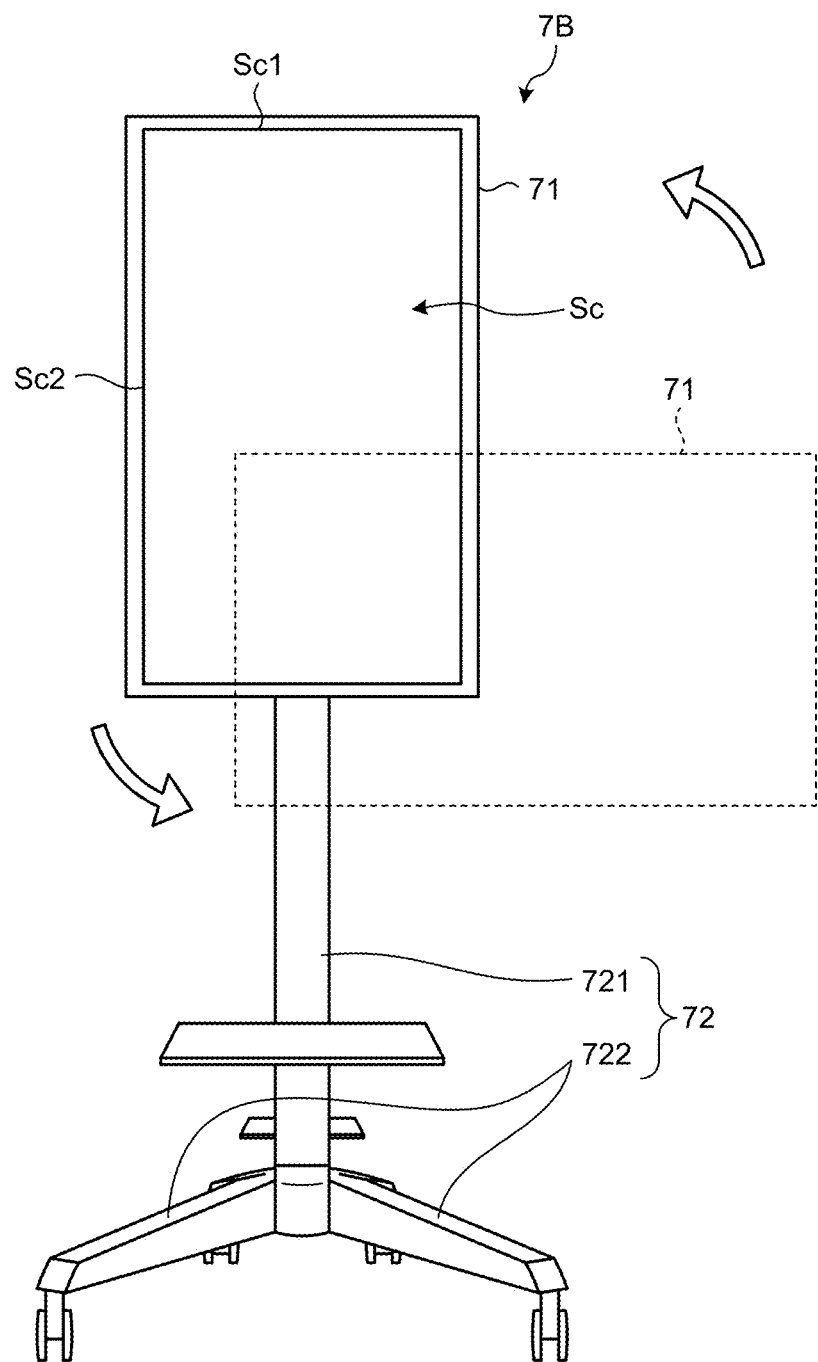
FIG. 11B is a diagram illustrating a modification of the first and second embodiments of the present disclosure.
Figure 12:
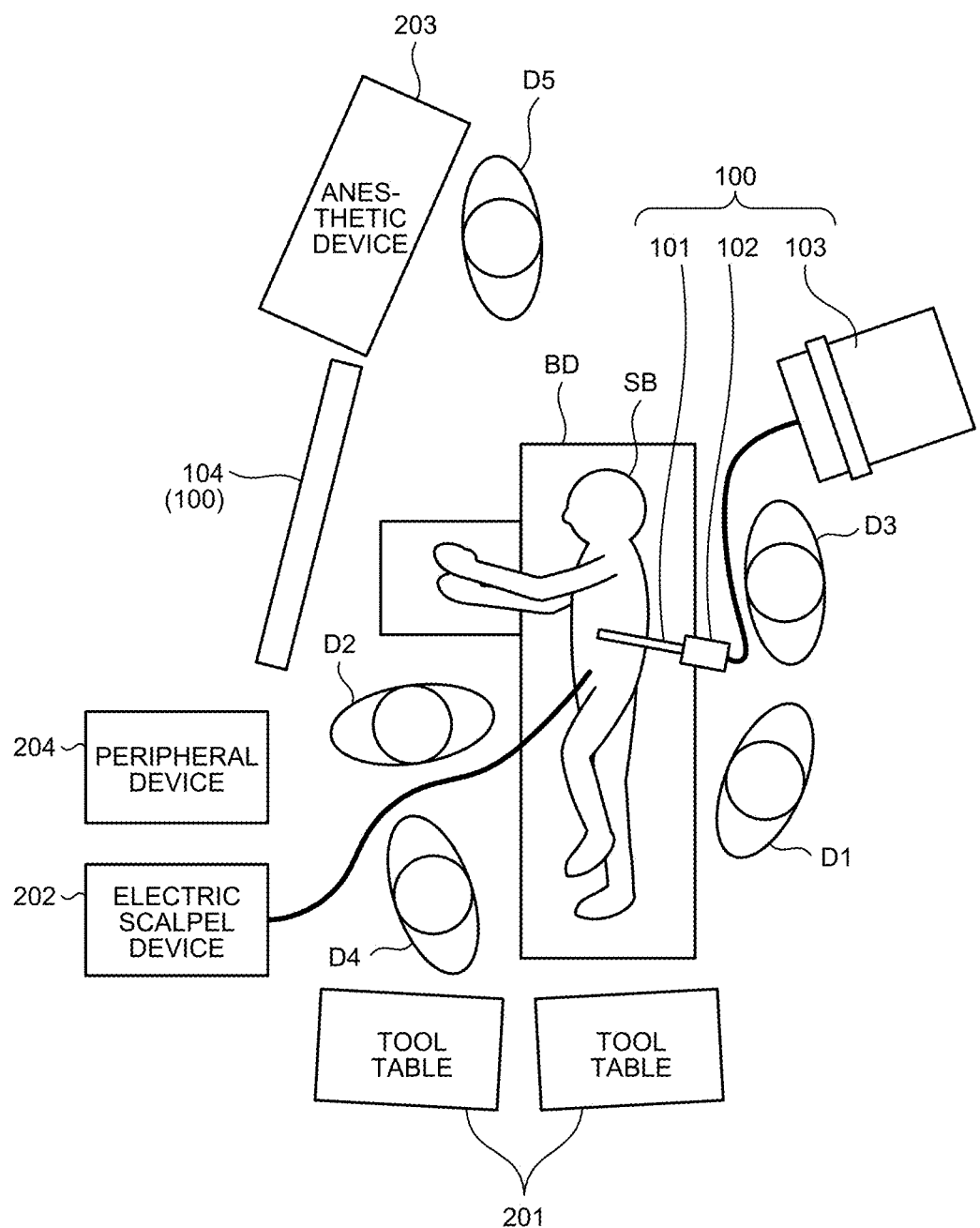
FIG. 12 is a diagram illustrating a configuration of an endoscope device in the related art.

FIGS. 11A and 11B are diagrams illustrating a modification of the first and the second embodiments of the present disclosure. Specifically, FIGS. 11A and 11B correspond to FIGS. 3A and 3B, respectively.

In the first and the second embodiments described above, the substantially center position on the back surface of the image display part 71 is connected to the pillar 721, and the image display part 71 is configured to be rotatable about the substantially center position on the back surface. However, the embodiment is not limited thereto. A display device 7B illustrated in FIG. 11A or FIG. 11B may be used.

In the display device 7B, one end in a longitudinal direction on the back surface of the image display part 71 is connected to the pillar 721, and the image display part 71 is configured to be rotatable about the one end in the longitudinal direction.

With such a configuration, as is clear from comparison between FIGS. 3B and 11B, a large space is created on one side in a horizontal direction (in FIG. 3B and FIG. 11B, the right side) of the image display part 71 when the setting state of the image display part 71 is changed from the horizontal arrangement state to the vertical arrangement state. Accordingly, a path of flow may be sufficiently secured for a person standing in the vicinity of the image display part 71.

In the first and the second embodiments described above, when the diameter DM of the subject image SI is larger than the reference threshold, the magnification/reduction ratio of the subject image SI in a case in which the image display part 71 is set in the vertical arrangement state is set to be smaller than the magnification/reduction ratio of the subject image SI in a case in which the image display part 71 is set in the horizontal arrangement state. However, the embodiment is not limited thereto. For example, a user may set the configuration to be switchable between the cases in which the magnification/reduction ratio of the subject image SI is smaller when the image display part 71 is set in the vertical arrangement state than the magnification/reduction ratio of the subject image SI when the image display part 71 is set in the horizontal arrangement state, and in which the magnification/reduction ratio of the subject image SI is the same when the image display part 71 is set in the vertical arrangement state as the magnification/reduction ratio of the subject image SI when the image display part 71 is set in the horizontal arrangement state.

In the first and the second embodiments described above, change of the setting state of the image display part 71 from the horizontal arrangement state to the vertical arrangement state may be limited in a case in which the diameter DM of the subject image SI is larger than the reference threshold. In such a case, the image display part 71 may be caused to display a message and the like for prohibiting change of the setting state from the horizontal arrangement state to the vertical arrangement state.

In the first and the second embodiments described above, rotation correction is performed on the subject image SI only when the image display part 71 is set in the vertical arrangement state, but the embodiment is not limited thereto. For example, a configuration may be employed for sequentially detecting a rotation angle at the time when the setting state of the image display part 71 is changed from the horizontal arrangement state to the vertical arrangement state, and sequentially performing rotation correction corresponding to the rotation angle. With such a configuration, in the observation image OF displayed during a period in which the horizontal arrangement state is changed to the vertical arrangement state, the up-and-down direction of the subject image SI is along the vertical direction.

A processing flow is not limited to a processing order in the flowchart (FIG. 6) explained in the first and the second embodiments, and may be modified without contradiction.

An algorithm of the processing explained using a flowchart in the present disclosure may be described as a computer program. Such a computer program may be recorded in a recording part inside a computer, or recorded in a computer-readable recording medium. The computer program may be recorded in the recording part or the recording medium when the computer or the recording medium is shipped as a product, or may be recorded therein by being downloaded via a communication network.

The image processing device for an endoscope according to the present disclosure processes the taken image including the subject image captured by the endoscope to generate the video signal, and outputs the video signal to the image display part. The image display part displays the observation image based on the video signal. The image display part is configured to be able to be set both in the first setting state (hereinafter, referred to as a horizontal arrangement state) in which the first side (hereinafter, referred to as a short side) of the display screen is along the vertical direction, and in the second setting state (hereinafter, referred to as a vertical arrangement state) in which the second side (hereinafter, referred to as a long side) of the display screen is along the vertical direction. The image processing device for an endoscope recognizes the setting state (the horizontal arrangement state or the vertical arrangement state) of the image display part, and generates the video signal so that the subject image in the observation image has an orientation corresponding to the setting state of the image display part.

That is, when the setting state of the image display part is changed from the horizontal arrangement state to the vertical arrangement state, the width of the display screen is reduced because the short side thereof is along the horizontal direction, so that the path of flow may be secured for a person standing in the vicinity of the image display part. When the setting state of the image display part is changed from the horizontal arrangement state to the vertical arrangement state, the subject image in the observation image has an orientation corresponding to the setting state of the image display part (the up-and-down direction of the subject image is along the vertical direction). Thus, after the path of flow is secured for the person standing in the vicinity of the image display part, there is no need to change the setting state of the image display part again from the vertical arrangement state to the horizontal arrangement state.

Accordingly, with the image processing device for an endoscope according to the present disclosure, cumbersome work of moving the setting place of the image display part is not required, so that convenience may be improved.

The endoscope device according to the present disclosure includes the image processing device for an endoscope described above, so that the endoscope device according to the present disclosure has the same effect as that of the image processing device for an endoscope described above. The image processing method of the image processing device for an endoscope according to the present disclosure is performed by the image processing device for an endoscope described above, so that the image processing method has the same effect as that of the image processing device for an endoscope described above. The image processing program according to the present disclosure is executed by the image processing device for an endoscope described above, so that the image processing program has the same effect as that of the image processing device for an endoscope described above.

It should be understood by those skilled in the art that various modifications, combinations, sub-combinations and alterations may occur depending on design requirements and other factors insofar as they are within the scope of the appended claims or the equivalents thereof.

What is claimed is:

1. An image processor for use with a medical device that outputs an image of a subject and an image display that has a first side shorter than a second side intersecting with the first side, and the image display having a first setting state in which the first side is along a vertical direction and a second setting state in which the second side is along the vertical direction, the image processor comprising:
circuitry configured to:
detect whether a current setting state of the image display is the first setting state or the second setting state;
process the image of the subject to generate a video signal such that the image of the subject to be displayed on the image display has an orientation corresponding to the current setting state of the image display; and
output information to be displayed along with the image of the subject, wherein
on condition that the current setting state is in the first setting state, the circuitry will automatically cause the information to be displayed at a first position on the image display relative to the image of the subject on the image display, and
on condition that the current setting state is in the second setting state, the circuitry will automatically cause the information to be displayed at a second position on the image display position, relative to the image of the subject on the image display.

2. The image processor according to claim 1, wherein, in the first setting state, the information is displayed in in a first region at the first position and a third region at a third position, different from the first and second positions, and, in the second setting state, the information is displayed in a second region at the second position.

3. The image processor according to claim 2, wherein a total area of the first and third regions is equal to the second region.

4. The image processor according to claim 1, wherein, in the first setting state, the information is displayed in in a first region at the first position and, in the second setting state, the information is displayed in a second region at the second position, wherein the first region is smaller than the second region.

5. The image processor according to claim 1, wherein, on condition that the current setting state is the first setting state, process the image of the subject to be displayed in a central region along a horizontal direction of the image display and the first position is at least one of a left side of the image of the subject and a right side of the image of the subject.

6. The image processor according to claim 1, wherein, on condition that the current setting state is the second setting state, process the image of the subject to be displayed in an upper region or a lower region along a vertical direction of the image display and the second position is in the lower region or the upper region not occupied by the image of the subject.

7. An endoscope device comprising:
an endoscope to be inserted into the subject;
a camera for the endoscope that is detachably connected to an eyepiece part of the endoscope to take the image of the subject, the endoscope and the camera being the medical device;
a controller that controls an operation of the camera;
the image processor according to claim 1; and
a display being the image display.

8. The endoscope device according to claim 7, wherein the image processor is part of the controller.

9. The endoscope device according to claim 7, wherein the image processor is part of the display.

10. The endoscope device according to claim 7, wherein the image display has a screen size of 40 inches or more.

* * * * *